(12) United States Patent
Bergmann et al.

(10) Patent No.: US 8,354,506 B2
(45) Date of Patent: Jan. 15, 2013

(54) ANTIBODIES FOR THE SELECTIVE DETERMINATION OF PROCALCITONIN 1-116

(75) Inventors: Andreas Bergmann, Berlin (DE); Joachim Struck, Berlin (DE)

(73) Assignee: B.R.A.H.M.S GmbH, Hennigsdorf (DE)

( * ) Notice: Subject to any disclaimer, the term of this patent is extended or adjusted under 35 U.S.C. 154(b) by 246 days.

(21) Appl. No.: 12/529,089

(22) PCT Filed: Feb. 21, 2008

(86) PCT No.: PCT/EP2008/001373
§ 371 (c)(1),
(2), (4) Date: Aug. 28, 2009

(87) PCT Pub. No.: WO2008/104321
PCT Pub. Date: Sep. 4, 2008

(65) Prior Publication Data
US 2010/0056763 A1     Mar. 4, 2010

(30) Foreign Application Priority Data
Feb. 28, 2007 (DE) .......................... 10 2007 009 751

(51) Int. Cl.
*C07K 16/26* (2006.01)
(52) U.S. Cl. .............. 530/387.1; 530/387.9; 530/388.23
(58) Field of Classification Search .................. None
See application file for complete search history.

(56) References Cited

U.S. PATENT DOCUMENTS

| | | | | |
|---|---|---|---|---|
| 5,639,617 A * | 6/1997 | Bohuon | .......................... | 435/7.1 |
| 2003/0108550 A1 | 6/2003 | Althaus et al. | ............. | 424/146.1 |

FOREIGN PATENT DOCUMENTS

| | | |
|---|---|---|
| EP | 0539477 | 7/1991 |
| EP | 0656121 | 8/1993 |
| WO | 00/22439 | 4/2000 |
| WO | 2007/009789 | 1/2007 |

OTHER PUBLICATIONS

Walter et al., Proc. Natl. Acad. Sci., USA 1980, 77:5197-5200.*
Harlow et al., Antibodies, A Laboratory Manual, 1988, pp. 75 and 76.*
E. O'Connor et al., "Serum Procalcitonin and C-reacive Protein as Markers of Sepsis and Outcome in Patients with Neurotrauma and Subarachnoid Haemorrhage", Anaesthesia and Intensive Care, Aug. 2004, vol. 32(4), 465-470.
John Whicher et al., "Procalcitonin as an acute phase marker", Ann Clin Biochem 2001; 38, 483-493.
K. L. Becker et al., "Procalcitonin and the Calcitonin Gene Family of Peptides in Inflammation, Infection, and Sepsis: A Journey from Calcitonin Back to Its Precursors", The Journal of Clinical Endocrinology & Metabolism, Apr. 2004, 89(4): 1512-1525.
Paresh Dandona et al., "Procalcitonin Increase after Endotoxin Injection in Normal Subjects", Journal of Clinical Endocrinology and Metabolism, 1994 vol. 79(5), 1605-1608.
Dominique Gendrel et al., "Procalcitonin as a marker for the early diagnosis of neonatal infection", The Journal of Pediatrics, 1996 vol. 128(4), 570-573.
Richard H. Snider, Jr., et al., "Procalcitonin and its Component Peptides in Systemic Inflammation: Immunochemical Characterization", Journal of Investigative Medicine, vol. 45(9), Dec. 1997, 552-560.
Kevin T. Whang et al., "Serum Calcitonin precursors in Sepsis and Systemic Inflammation*", Journal of Clinical Endocrinology and Metabolism, 1998 vol. 83(9), 3296-3301.
Beat Müller et al., "Calcitonin precursors are reliable markers of sepsis in a medical intensive care unit", Critical Care Med 2000, vol. 28(4), 977-983.
Wolfgang Weglöhner et al., "Isolation and characterization of serum procalcitonin from patients with sepsis", Peptides 22 (2001) 2099-2103.
S. Wrenger et al., "Amino-terminal truncation of procalcitonin, a marker for systemic bacterial infections, by dipetidyl peptidase IV (DP IV)", FEBS Letters, 466 (2000) vol. 155-159.
Nils Morgenthaler et al., "Sensitive Immunoluminometric Assay for the Detection of Procalcitonin", Clinical Chemistry 48(5), 2002, 788-790.
International Search Report with Written Opinion for priority application International Application No. PCT/EP2008/001373.
Marcel Assicot et al., "High Serum Procalcitonin Concentrations in Patients with Sepsis and Infection", The Lancet, vol. 341, Feb. 27, 1993, pp. 515-518.

* cited by examiner

*Primary Examiner* — Prema Mertz
(74) *Attorney, Agent, or Firm* — Heslin Rothenberg Farley & Mesiti P.C.

(57) ABSTRACT

The present invention provides an immunodiagnostic method for determining procalcitonin and procalcitonin derivatives in a biological sample of a patient for diagnostic purposes, in particular in the monitoring and control of treatment and the monitoring of the progression of a local or systemic bacterial infection, inflammation, sepsis or neurodegenerative disease. In particular, the method detects molecular forms of procalcitonin, or procalcitonin partial peptides derived therefrom, having the amino acids alanine and proline (Ala-Pro, AP) in positions 1 and 2 of the amino terminus of the complete procalcitonin 1-116 (SEQ ID NO: 1.) Also disclosed are antibodies and kits for carrying out such a method.

4 Claims, 4 Drawing Sheets

ANTIBODIES FOR THE SELECTIVE DETERMINATION OF PROCALCITONIN 1-116

CROSS REFERENCE TO RELATED APPLICATIONS

This application is a 371 filing of PCT International application no. PCT/EP2008/001373 filed Feb. 21, 2008 and published in English as WO 2008/104321 A1 on Sep. 4, 2008, which claims the priority of German application no. 102007009751.6 filed Feb. 28, 2007. The disclosures of these applications and all other patents, published applications and other references cited herein are hereby incorporated by reference in their entirety.

The invention relates to the area of medical diagnosis, in particular the determination of biomarkers in biological fluids by means of immunodiagnostic methods. More precisely, the invention relates to the determination of the peptide procalcitonin for diagnostic purposes, a selective measured value not obtainable to date being determined for the complete procalcitonin 1-116 and being used in particular for a more sensitive early diagnosis, monitoring of treatment and monitoring of the progression of systemic and local infections, in particular of bacterial infections and of sepsis.

In the context of the present invention, terms such as "diagnosis" or "for diagnostic purposes" are used as a general term for medical determinations which may arise out of different problems depending on the clinical condition of the patient from which the determination is carried out and which serve in particular for the diagnosis and early diagnosis, the determination of severity and the assessment of the progression, including the treatment-accompanying assessment of the progression, and the prognosis of the future progression of a disease and the risk stratification of patients. Even if, in the following description, particular attention is made to improved monitoring of progression and treatment, no limitation of the term "for diagnostic purposes" to such specific diagnostic aims is associated therewith.

The mature prohormone procalcitonin (PCT) is a peptide which consists of 116 amino acids and was first discussed as precursor of the important hormone calcitonin (thyreocalcitonin) and the complete amino acid sequence of which (SEQ ID NO: 1) has long been known, as have the details of its normal proteolytic degradation, which leads to the liberation of the mature hormone calcitonin and other shorter peptides, including in particular so-called katacalcin (procalcitonin 96-116) and an N-terminal peptide (N-procalcitonin 1-57), which are designated herein, inter alia, as "PCT partial peptides". As explained more exactly, for example, in the patents EP 0 656 121 B1 or U.S. Pat. No. 5,639,617 of the Applicant and in publications such as ASSICOT M., GENDREL D., CARSIN H., RAYMOND J., GUILBAUD J., BOHOUN C. (1993): High serum Procalcitonin concentrations in patients with sepsis and infection. Lancet 341:515-518, severe bacterial infections and certain parasitic and fungal infections with a systemic inflammatory reaction induce the liberation of PCT in the circulation, where it is found in very high, readily measurable amounts (cf. for example also the overview articles in O'CONNOR E., VENKATESH B., LIPMAN J., MASHONGONYIKA C., HALL J. (2001): Procalcitonin in critical illness. Critical Care and Resuscitation 3:236-243; WHICHER I., BIENVENU J., MONNERET G. (2001): Procalcitonin as an acute phase marker. Annals of Clinical Biochemistry 38:483-893; BECKER K. L., NYLEN E. S., WHITE J. C., MUELLER B., SNIDER R. H. (2004): Procalcitonin and the calcitonin gene family of peptides in inflammation, infection and sepsis: a journey from procalcitonin back to its precursors. Journal of Clinical Endocrinology and Metabolism 89: 1512-1525). Viral, autoimmune and allergic diseases on the other hand do not lead to a significant increase in the measurable PCT concentration in the blood. PCT reflects the severity of a bacterial infection and is used as a marker for the diagnosis and the therapeutic monitoring of sepsis, severe sepsis and septic shock of bacterial origin (DANDONA P., NIX D., WILSON M. F., ALJADA A., LOVE J., ASSICOT M., BOHUON C. (1994): Procalcitonin increase after endotoxin injection in normal subjects. Journal of Clinical Endocrinology and Metabolism 79:1605-1608; GENDREL D., ASSICOT M., RAYMOND J., MOULIN F., FRANCOUAL C., BADOUAL J., BOHOUN C. (1996): Procalcitonin as a marker for the early diagnosis of neonatal infection. Journal of Paediatrics 128:570-573; SNIDER R. H. JR., NYLEN E. S., BECKER K. L. (1997): Procalcitonin and its component peptides in systemic inflammation: immunochemical characterization. Journal of Investigative Medicine 45:552-560; WHANG K. T., STEINWALD P. M., WHITE J. C., NYLEN E. S., SNIDER R. H., SIMON G. L., GOLDBERG R. L., BECKER K. L. (1998): Serum calcitonin precursors in sepsis and systemic inflammation. Journal of Clinical Endocrinology and Metabolism 83:3296-3301; MUELLER B., BECKER K. L., SCHACHINGER H., RICKENBACHER P. R., HUBER P. R., ZIMMERLI W., RITZ R. (2000): Calcitonin precursors are reliable markers of sepsis in a medical intensive care unit. Critical Care Medicine 28:977-983). The general technical knowledge recorded in said patents and literature references is expressly referred to for supplementing the present description.

The determination of PCT can also be used for differential diagnostic purposes since, on the basis of the measurable PCT concentrations in serum and plasma, it is possible to distinguish inflammatory diseases based on bacterial infections from those of non-infectious etiology (cf. also EP 0 880 702 B1). This possibility of distinguishing has proved to be very valuable for controlling the use of antibiotics in the treatment, in that it is possible to avoid administering antibiotics also in cases where they are not effective because the patient does not have a bacterial infection.

Attempts have also already been made to determine procalcitonin in the case of infections in the cerebrospinal fluid (CSF). In all cases described in the literature, a commercial assay developed for sepsis diagnosis and having a functional assay sensitivity (FAS) of only 300 ng/l was employed. The measured results obtained were contradictory. As described in the patent application DE 10 2005 034 174.8 just published or in WO 2007/009789, however, more significant measured results can be obtained if a more sensitive assay is employed, which has also been available for some time. With such an assay, a significant correlation of the measurable PCT immunoreactivity with the severity of the disease is obtained even in the case of neurodegenerative diseases. Even if the determination of PCT in CSF is not specifically discussed below, it is expressly within the scope of the present invention to use the method according to the invention which is described herein also in this partial area of diagnostics.

A determination in urine is in principle also covered by the present invention.

The determination of PCT is effected, as described in the abovementioned patents and literature references, in a suitable manner by immunoassays of the sandwich type with the use of two antibodies which bind to the amino acid sequence of the complete PCT peptide so that the PCT processed completely with liberation of calcitonin is not detected but the total unprocessed PCT and optionally also those longer PCT partial peptides which still have both binding sites for the two antibodies used in a sandwich assay within a single molecule are detected, it not being possible to distinguish between optionally terminally modified PCT forms. Conventional methods employ two antibodies which in general bind to those segments of the complete PCT peptide which, on proteolytic processing of PCT with formation of calcitonin, come to be located on different PCT partial peptides among the PCT partial peptides formed or which are located on PCT partial peptides which do not comprise the calcitonin sequence.

The fact that the complete PCT 1-116 (SEQ ID NO: 1) is not found or at least not primarily found in serum or plasma in the case of sepsis but instead a PCT 3-116 which is shorter by two amino acids (SEQ ID NO: 2) is explained in EP 1 121 600 A1 or EP 1 408 334 A1 or U.S. Pat. No. 6,756,483, which is referred to for supplementing the present description. Furthermore, in this context, reference is made to the publication: WEGLÖHNER W, STRUCK J, FISCHER-SCHULZ C, MORGENTHALER N G, OTTO A, BOHUON C, BERGMANN A: Isolation and characterization of serum procalcitonin from patients with sepsis. Peptides 2001; 22: 2099-103. As explained in said publications, the only biomolecule with procalcitonin immunoreactivity which was characterizable in the investigated samples from sepsis patients was procalcitonin 3-116 mentioned (SEQ ID NO: 2). In the further work: WRENGER S, KAHNE T, BOHUON C, WEGLÖHNER W, ANSORGE S, REINHOLD D: Amino-terminal truncation of procalcitonin, a marker for systemic bacterial infections, by dipeptidyl peptidase IV (DP IV); FEBS Lett 2000; 466:155-9, it is shown that this procalcitonin 3-116 can be obtained from a synthetically prepared procalcitonin 1-116 by the action of dipeptidyl-aminopeptidase IV (DAP IV; DP IV; CD 26; E.C. 3.4.14.5).

None of said publications reveals whether the procalcitonin 3-116 characterized in the case of sepsis and infections is directly secreted or whether it is subsequently formed proteolytically from a "complete" precursor in the form of procalcitonin 1-116 (PCT 1-116) released as an intermediate into the circulation. Said publications reveal just as little regarding whether a "complete procalcitonin" 1-116 occurs in measurable steady-state concentrations in the biological samples investigated (whole blood or serum or plasma) or whether it makes a significant contribution to the measured signal obtained in the conventional procalcitonin determination.

For the determination of the procalcitonin immunoreactivities in serum/plasma, there are various commercial assays of the Applicant, e.g. the chemiluminescence assay B.R.A.H.M.S PCT LIA (B.R.A.H.M.S AG), which has an FAS of about 300 ng/l and is tailored to PCT determination in sepsis, where very high PCT concentrations may occur. For PCT determination with higher sensitivity, a modified sandwich immunoassay was recently developed which operates with an affinity-purified polyclonal antibody and which is described in more detail in MORGENTHALER N. G., STRUCK J., FISCHER-SCHULZ C., BERGMANN A. (2002): Sensitive immunoluminometric assay for the detection of procalcitonin. Clinical Chemistry 48: 788-789, and is available as B.R.A.H.M.S PCTsensitiv LIA (B.R.A.H.M.S AG). This assay has a substantially better functional assay sensitivity (FAS) of 7 ng/l. With the aid of this assay, it was possible to determine a mean PCT serum concentration of 13.5 ng/l (13.5 pg/ml) in healthy persons, values from <7 to 63 ng/l having been found and the 97.5% percentile being at 42.5 ng/l.

In order to enable the hospital physician to carry out a rapid check of the status of a potential sepsis patient directly in hospital ("point-of-care"), a one-step fast test in the form of an immunochromatographic assay for rapid semi-quantitative determination of procalcitonin in human serum or human plasma of a patient is available (PCT-Q; B.R.A.H.M.S Aktiengesellschaft).

As is evident, for example, from the publications and overview articles cited above, the determination of the biomarker procalcitonin is now firmly established in chemical routine, primarily for early diagnosis of sepsis. A reason for this success is a reliable correlation between sepsis or bacterial infections and an increase in the measurable PCT immunoreactivity in the blood or serum/plasma of the patients, and relatively simple measurability of this PCT immunoreactivity owing to the high concentrations which are reached in the blood of sepsis patients, due to the high stability of the PCT 3-116 at least primarily detected in the measurement.

In spite of these indisputable advantages of the determination of the PCT immunoreactivity by the assays available to date for this purpose, however, the inventors discovered that the high stability and the high concentrations of the measured PCT immunoreactivity are also associated with certain disadvantages for certain clinically relevant diagnostic problems:

A high stability or "long life" of an analyte, e.g. of a peptide such as PCT 3-116, means that the measurement of such an analyte provides summary information about the already elapsed secretory activities for a relatively long period. If, for example, more or less continuous production of an analyte during an acute pathological process is assumed, the stable analyte accumulates in the biological sample, and its past physiological production is reflected cumulatively in its measurable concentrations, but reduced by its concentration reduction which has taken place in the same period at its physiological clearance rate (its disappearance from the sample owing to its conversion into degradation products which are not detectable analytically, its excretion via the kidneys or owing to other physiological mechanisms known per se). The more long-lived an analyte or the lower its clearance rate, the smaller is the influence of the exact measuring time on the determination of the abovementioned "formation" or "secretion" of the analyte. For example, in this picture, a concentration which is constant for relatively long periods may mean that formation and clearance balance one another. If the concentration decreases, this may indicate that the secretion of the analyte, which acts in the sense of "concentration replenishment", has decreased. Nevertheless, the concentration of the analyte in the blood may still have high values. If, however, the measurable concentration values are high and the clearance rate low, changes in the secretion of an analyte manifest themselves only as relatively small, poorly interpretable changes of relatively large numbers.

If, however, the clinician is interested precisely in rapidly establishing changes in the secretion of the analyte, for example because he wishes to draw conclusions about the success of a treatment or recurrence or reinfection on the basis of these changes, it is frequently difficult to recognise such a change rapidly and unambiguously on the basis of the measured concentration values of "long-lived" analytes.

The inventors therefore set themselves the object of improving the determination of procalcitonin in the sense that changes of the procalcitonin secretion can be recognised rapidly and reliably so that the periods for recognition of the success of a treatment or the introduction of necessary therapeutic interventions are shorter and that it is possible to obtain additional, previously unavailable information which immediately permits conclusions about how far an infection/sepsis has already progressed when the physician has to assess the patient for the first time.

Further important features of the present invention are evident to the person skilled in the art from the following description and the explanations of the examples, in particular from the discussions of the measured results given, these explanations and examples hereby being incorporated by reference.

At the beginning of the inventors' considerations, it was assumed that the peptide procalcitonin, which is determined as PCT immunoreactivity by the conventional assay methods, is presumably formed from its associated prepeptide (preprocalcitonin; pre-PCT) having 141 amino acids, the amino acid sequence of which is known (SEQ ID NO: 3). As is generally known for many prohormones, PCT is formed from this longer precursor molecule by elimination of the signal sequence. Although the cleavage point has not been determined experimentally, signal sequences generally have similar patterns, so that cleavage points can be predicted with high probability. In the case of pre-PCT, the signal sequence should comprise the amino acids 1 to 24 of pre-PCT (SEQ ID NO: 3). It follows from this that the amino-terminal amino acid in position 1 of the prohormone PCT corresponds to the amino acid 25 of pre-PCT (SEQ ID NO: 3). On the basis of such considerations, it was originally assumed that the PCT found in the circulation during sepsis comprises 116 amino acids after elimination of the signal sequence and has the amino acid sequence PCT 1-116 (SEQ ID NO: 1). Since, however, only PCT 3-116 (SEQ ID NO: 3) could be characterized in samples in sepsis patients, there remained the question of intermediate secretion of PCT 1-116 and the possibly achieved concentrations of such a PCT 1-116 in the circulation. It should once again be pointed out that the assays of the sandwich type which have been used to date for determining procalcitonin immunoreactivity operate with combinations of two antibodies which do not permit a distinction between PCT 1-116 and 3-116. The known assays therefore cannot of course selectively detect said different forms of PCT, and they therefore also do not detect possible characteristic changes in the relative molar amounts of said analytes if such changes occur in the course of a pathological process, for example in the course of a sepsis. The PCT immunoreactivity determined by a conventional assay is therefore also referred to as "PCT total" in the present application.

The inventors decided in this situation to provide a novel type of method for the immunodiagnostic determination of procalcitonin, by means of which only those procalcitonin fractions which also have the first two amino acids of procalcitonin 1-116 are selectively determined, and, with the use of this novel method, to check whether it is possible therewith to obtain clinically relevant measured results which are qualitatively better than the results of the prior determination of procalcitonin immunoreactivity.

As described in more detail in the following experimental part, the inventors first developed novel antibodies having the binding properties required for a clinical determination, so that they recognise only those procalcitonin molecules which contain the complete procalcitonin sequence at the amino terminus with the first two amino acids (Ala-Pro) of procalcitonin 1-116 or which contain at least amino acid 2 (Pro). They then used these novel antibodies in an assay of the sandwich type which permits a selective determination of the PCT 1-116 in a biological sample of a human patient, for example in serum or in particular in plasma, without the measured value being influenced by the presence of PCT 3-116 (SEQ ID NO: 2) in the sample. In other words, the concentrations of PCT 3-116, and of course of all other PCT fragments truncated at the N-terminus by at least two amino acids, if present in the biological sample, are not detected (co-determined) by the assay method according to the present invention for the selective determination of PCT 1-116 in a biological sample and do not become part (do not form a significant increment) of the measured value.

As shown below in the experimental part of the Application, the measured results obtained using such an assay fulfilled the hopes of the inventors for the desired improvement of the diagnostic determination of procalcitonin for the abovementioned particular diagnostic purposes.

It was in fact found that significant, readily measurable concentrations of PCT 1-116 are present in fresh samples of human serum and in particular of fresh human plasma of patients. The molar concentrations of PCT 1-116 found by the inventors in such samples are in the range of about 1/5 to 1/8 of the molar concentrations for the PCT immunoreactivity measurable in parallel by traditional methods ("PCT total").

If it is assumed that the total PCT secreted in the circulation is secreted primarily as PCT 1-116, it follows that the concentrations of PCT 1-116 and of PCT total must be equal at a hypothetical time at the beginning of the PCT secretion so that a maximum hypothetical initial limit of 1.0 can be assumed for the ratio of PCT 1-116 to PCT total. Ratios in the range of about 1/5 to 1/8, as were found by the inventors in the samples investigated; therefore already contain per se information about the history of the sample, for example in the sense of the elapsed duration and/or severity of the infection/sepsis. Owing to the lower stability of PCT 1-116 (because of the conversion into PCT 3-116), said ratio and the concentration changes which can be established for PCT 1-116 reflect the acute status of a patient very much more directly than the values for the more stable PCT 3-116. The selective determination of PCT 1-116 therefore leads to considerable diagnostic progress. This also manifests itself in particular when the selective determination according to the invention of the PCT 1-116 with the aid of the novel method is combined with the conventional determination of the total PCT immunoreactivity (PCT total).

The method according to the invention has particular advantages in cases where a rapid detection of the actual disease status of a patient is desirable. In principle, however, it can be used in all cases where the known methods have been used to date for determining the PCT immunoreactivity. As long as a determination is selective for PCT 1-116 with both amino-terminal amino acids (Ala-Pro) or at least for a procalcitonin with the amino acid in position 2 (Pro), the method is to be considered as one according to the present invention. The special assay form chosen plays a fairly minor role, and a special assay format is chosen primarily from practical points of view relating to measurement technology.

Although a specific method of the sandwich type with the use of specific antibodies (monoclonal antibodies) is therefore described in the experimental part of this Application and used for the measurement, the present invention is not limited to this specific method or a method of a similar type. Rather, it includes any desired immunodiagnostic methods which, in the context of the present invention, permit a selective determination of PCT 1-116 without the measured value being influenced by simultaneously present other PCT derivatives, in particular PCT 3-116. In other words, the concentrations of PCT 3-116 in the biological sample do not contribute to, or change, the value selectively measured for PCT 1-116.

It is self-evident to the person skilled in the art that, for example, assays of the competitive type (for example with an immobilized selective antibody and a marked/selectively markable analogue of the analyte which competes with PCT 1-116; or with an immobilized analogue and a marked selective antibody) or other assay formats, for example so-called turbidimetric assays, can also be used instead of the assay of the sandwich type described.

In principle, any known marker suitable for diagnostic assays can be used (i.e. instead of the luminescence marking used in the examples, for example, radioisotopes, enzymes, fluorescence labels, other chemoluminescence labels or bioluminescence labels and directly optically detectable colour markings, such as, for example, gold atoms and dye particles, as used in accelerated tests, can also be used).

It is furthermore expressly within the scope of the present invention to design the method according to the invention as an accelerated test, for example in the form of an immunochromatographic assay method.

If the method is designed as a heterogeneous method in which a specific binder in immobilized form is present bound to a solid phase and/or the reaction products are at least partly immobilized on a solid phase, the solid phase may be any desired suitable solid phase, for example a wall of a test tube, a particulate solid phase, for example in the form of magnetic particles suspended in the reaction solution, or a solid phase in the form of a support of an immunochromatographic apparatus (for an accelerated test).

In a currently preferred embodiment, the method is carried out as a heterogeneous sandwich immunoassay in which one of the antibodies is immobilized on the walls of coated test tubes (e.g. of polystyrene; "coated tubes"; CT) or on microtitre plates, for example of polystyrene, or on particles, for example magnetic particles, while the other antibody carries a residue which represents a directly detectable label or permits a selective link with a label and serves for detection of the sandwich structures formed. Delayed or subsequent immobilization with the use of suitable solid phases is also possible.

The method need not however be designed as a heterogeneous method in which at least one specific binder is present in immobilized form. All reactants and reaction products can also be present suspended in a homogeneous liquid phase and can remain there for the measurement. In such a case it is preferable to mark both antibodies used for the determination with parts of a detection system which permits signal generation or signal triggering when both antibodies are integrated into a single sandwich. Such techniques can be designed in particular as fluorescence amplification or fluorescence extinction detection methods. A particularly preferred method of this type relates to the use of detection reagents to be used in pairs, as described, for example, in U.S. Pat. No. 4,822,733, EP-B1-180 492 or EP-B1-539 477 and the prior art cited therein. They permit a measurement which selectively detects only reaction products which contain both marking components in a single immune complex, directly in the reaction mixture. As an example, reference may be made to the technology offered under the brands TRACE® (Time Resolved Amplified Cryptate Emission) or KRYPTOR®, which implement the teachings of the abovementioned applications.

It is furthermore assumed that the assay method according to the invention can advantageously also be used as part of a so-called multi-parameter diagnosis. Further parameters determined thereby are, for example, sepsis and infection parameters which may be selected, for example, from a group which consists of anti-ganglioside antibodies, the proteins total procalcitonin (PCT total), procalcitonin 3-116, CA 125, CA 19-9, S100B, S100A proteins, LASP-1, soluble cytokeratin fragments, in particular CYFRA 21, TPS and/or soluble cytokeratin-1 fragments (sCY1F), the peptides inflammin and CHP, other peptide prohormones, such as, in particular, pro-ANP, pro-BNP, pro-adrenomedullin, pro-endothelin, pro-vasopressin and the diagnostically usable peptide fragments thereof, glycine N-acyl transferase (GNAT), carbamoyl phosphate synthetase 1 (CPS 1) and the C-reactive protein (CRP), cytokines, e.g. of the interferon type, or suitable fragments thereof. In said multi-parameter determinations, it may be intended to determine the measured results for a plurality of parameters simultaneously or in parallel and to evaluate them, for example, with the aid of a computer program which also uses diagnostically significant parameter correlations.

A particularly important combination measurement is a parallel selective measurement of PCT 1-116 and the customary PCT immunoreactivity (PCT total), which, in the light of the results of the present Application, represents a summary measurement of the concentrations of PCT 1-116 plus PCT 3-116 present in a sample. Regarding the advantages of such a measurement, reference is expressly made to the following examples.

It is furthermore possible to combine selective measurements of PCT 1-116 and PCT 3-116. The inventors have also carried out such combination measurements with the use of a monoclonal antibody selective for PCT 3-116 (results not shown). Since the concentrations of PCT 3-116 constantly newly formed in the proteolytic degradation of PCT 1-116 are directly included in the concentrations of PCT 3-116, the evaluation of the comparative measurements is, however, more complex. In addition, it appears that a further proteolytic degradation may occur at the amino terminus of PCT 3-116, with the result that the measured results are falsified. A combination measurement of PCT 1-116 with a selective measurement of PCT 3-116 is therefore currently less preferable.

In the following examples, reference is made to figures in which.

EXPERIMENTAL PART

I. Assay Development

Peptide Syntheses and Antibody Development

I.1. Peptide Syntheses

Figure 1:
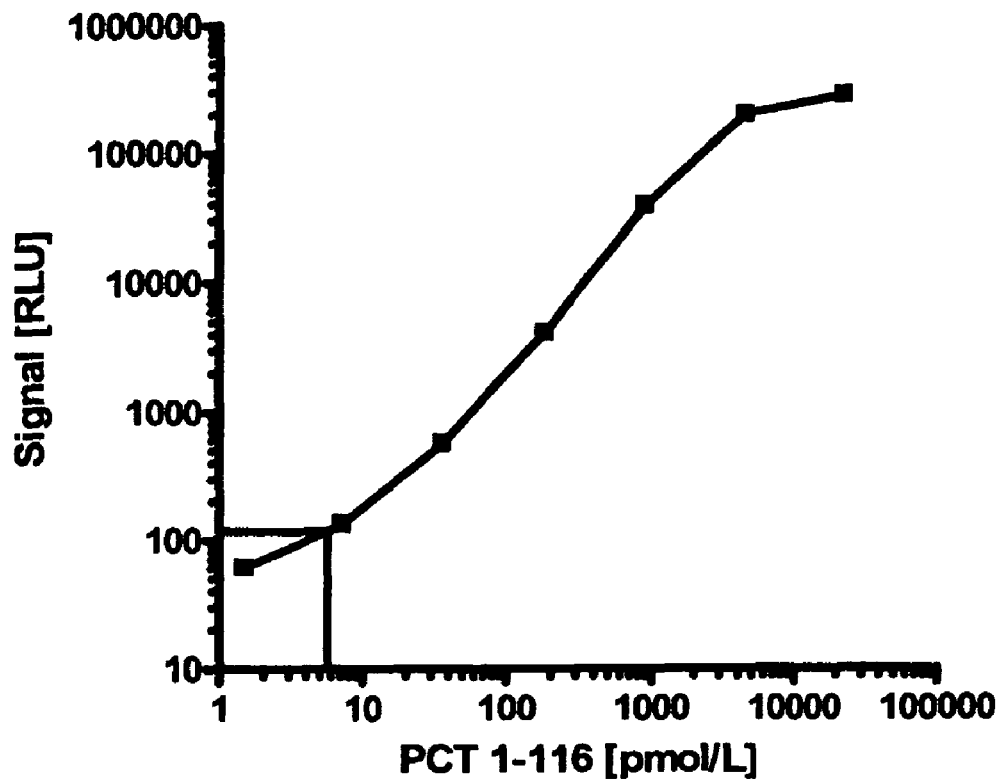
FIG. 1 shows a standard curve of a sandwich assay for the selective determination of PCT 1-116, as described in more detail in the experimental part.

The following peptides were synthesised as antigen constituents for antibody production, as selective binding partners for affinity purification and for epitope mapping and as potential standards and competitors:

Derived from the known amino acid sequence of pre-procalcitonin (pre-PCT; SEQ ID NO:3), a plurality of partial peptide segments were selected and were chemically synthesised as soluble peptides by standard methods. These were purified, subjected to quality control by means of mass spectrometry and reversed phase HPLC and lyophilized in aliquots (JPT, Berlin, Germany). The amino acid sequences of the peptides synthesised are (the stated amino acid positions are based on pre-PCT; amino acid 25 corresponds to amino acid 1 of PCT 1-116 according to SEQ ID NO: 1):

| | | | |
|---|---|---|---|
| PAS10 | APFRSALESC | 25-33 (+C-terminal cysteine) | (SEQ ID NO: 4) |
| PAD21 | AAPFRSALESSPADPATLSED | 24-44 | (SEQ ID NO: 5) |
| PAD20 | APFRSALESSPADPATLSED | 25-44 | (SEQ ID NO: 6) |
| PPD19 | PFRSALESSPADPATLSED | 26-44 | (SEQ ID NO: 7) |
| PFD18 | FRSALESSPADPATLSED | 27-44 | (SEQ ID NO: 8) |
| PRD17 | RSALESSPADPATLSED | 28-44 | (SEQ ID NO: 9) |
| PSD16 | SALESSPADPATLSED | 29-44 | (SEQ ID NO: 10) |
| PAN40 | APFRSALESSPADPATLSEDMSSD LERDHRPHVSMPQNAN | 25-44/122-141 | (SEQ ID NO: 11) |

I.2. Development, Marking and Characterization of Antibodies with Specificity for the N-Terminus of PCT 1-116

I.2.1. Development and Selection of Monoclonal Antibodies

Monoclonal antibodies were developed by standard methods, as described, for example, by Harlow and Lane (Harlow E., Lane D. "Antibodies—A Laboratory Manual", Cold Spring Harbor Laboratory, 1988, ISBN 0-87969-314-2). The development is summarized in more detail below:

By means of MBS (m-maleimidobenzoyl-N-hydroxysuccinimide ester), the peptide PAS10 (SEQ ID NO: 4; amino acids 1 to 9 of PCT 1-116) was conjugated with the carrier protein KLH (keyhole limpet haemocyanine) (cf. operating instructions "NHS-Esters-Maleimide Crosslinkers" from PIERCE, Rockford, Ill., USA). Balb/c mice were immunized with this conjugate. After boosting, spleen cells of the mice were subsequently fused with SP2/0 myeloma cells.

For binding tests of the antibodies from the culture supernatants of the myeloma cells, the peptides PAD20 (SEQ ID NO: 6 and PPD19 (SEQ ID NO: 7; amino acids 2-20 of PCT 1-116) were immobilised on microtitre plates. For this purpose, the peptides were dissolved in 20 m/M Na phosphate, pH 7.4, 50 mM NaCl in a concentration of 7 μg/ml, and 150 μl thereof were pipetted per cavity.

Incubation was effected for 20 hours at 4° C. The solution was filtered with suction. Each cavity was then filled with 150 μl of 10 mM sodium phosphate, 2% Karion FP, 0.3% bovine serum albumin, pH 6.5. After 20 hours the solution was filtered with suction.

150 μl of each of the culture supernatants to be tested were pipetted into microtitre plate cavities coated with PAD20 (SEQ ID NO: 6) or PPD19 (SEQ ID NO: 7). Incubation was effected for two hours at 22° C. The supernatant was filtered with suction. Washing was effected twice with 20 mM Na phosphate, pH 7.4, 50 mM NaCl, and bound antibodies were detected with secondary anti-mouse antibody-alkaline phosphatase conjugate by standard methods (SIGMA, Deisenhofen, Germany).

Those cell cultures which secreted antibodies which had bound to the peptide PAD20 (SEQ ID NO: 6) but far less to the peptide PPD19 (SEQ ID NO: 7) were selected for isolation. Culture supernatants from the isolations were screened by the same method as the initial cell cultures. Cell clones screened positively in this sense were then cultivated on a larger scale, and the antibodies were purified by means of affinity chromatography on a protein G column, and three of said antibodies were further investigated as potential candidates for the selective binding of PCT 1-116 in an immunoassay (internal designations of the antibodies: mAb 295/3H12; mAb 295/4G9; mAb 295/4611).

I.2.2. Marking of the Antibodies

For characterization of the epitope specificity of the three selected antibodies and subsequent assay development, the monoclonal antibodies obtained were marked with a chemiluminescence label as follows:

Each antibody was adjusted to a concentration of 1.5 mg/ml in a 100 mM potassium phosphate buffer (pH 8.0). 67 μl of the antibody solution were mixed with 10 μl of MA70 acridinium NHS ester (1 mg/ml; from HOECHST Behring) and incubated for 15 minutes at room temperature. Thereafter, 423 μl of 1 M glycine were added and incubation was effected for a further 10 minutes. Thereafter, the marking batch was re-buffered over an NAP-5 gel filtration column (Pharmacia) in 1 ml of mobile phase A (50 mM potassium phosphate, 100 mM NaCl, pH 7.4) according to the operating instructions and freed thereby from low molecular weight constituents. For separating off the last residues of labels not bound to antibody, gel filtration HPLC was carried out (column: Waters Protein Pak SW300). The sample was applied and was chromatographed at a flow rate of 1 ml/min with mobile phase A. The wavelengths 280 nm and 368 nm were measured using a flow photometer. The absorption ratio 368 nm/280 nm as a measure of the degree of marking of the antibody was 0.10+/−0.01 at the peak. The monomeric antibody-containing fractions (retention time 8-10 min) were collected and were collected in 3 ml of 100 mM sodium phosphate, 150 mM NaCl, 5% bovine serum albumin, 0.1% sodium azide, pH 7.4.

I.2.2. Epitope Mapping of Three Selected Monoclonal Antibodies

For the epitope mapping of the three developed and selected monoclonal antibodies, various peptides which represent the N-terminal segment of procalcitonin (cf. 1.1.; Tab. 1) were immobilized on tubes. This was effected as described above for the coating of microtitre plates, except that 300 μl of peptide solution were pipetted instead of 150 μl.

The respective chemiluminescence-marked monoclonal antibody was diluted in assay buffer (100 mM sodium phosphate, 150 mM NaCl, 0.5% bovine serum albumin, 0.1% unspecific mouse IgG, 0.1% sodium azide, pH 7.4), so that an end concentration of 0.9 million RLU (relative light units)/200 μl was obtained. 200 μl portions of these solutions were pipetted into the peptide tubes, and incubation was effected for 2 hours at 22° C. with shaking. This was followed by washing four times with 1 ml portions of wash solution (0.1% Tween 20) per tube, allowing to drip and measurement of the chemiluminescence bound to the tube in a luminometer (from BERTHOLD, LB952T; base reagents from BRAHMS AG).

As is evident from the following table 1, all three selected antibodies (internal designation mAb 295/3H12; mAb 295/4G9; mAb 295/4G11) reacted best with a peptide derived from pre-procalcitonin (or procalcitonin) if this ended with position 25 at the N-terminus (peptide PAD20; SEQ ID NO: 6). If position 25 was absent (peptide PPD19; SEQ ID NO: 7), only marginal binding was achieved, which accounted for only about twice the unspecific binding for the individual monoclonal antibodies and was lower by a factor of 199 (mAb 295/3H12), a factor of 85 (mAb 295/4G9) or a factor of 102 (mAb 295/4G11) than for peptide PAD20 in which position 25 was present.

The antibodies are thus highly specific and suitable for distinguishing procalcitonin peptides which contain positions 1 and 2 of PCT 1-116 (positions 25 and 26 of pre-PCT) at the N-terminus from those procalcitonin peptides which are shortened by only one amino acid residue at the N-terminus in comparison therewith.

TABLE 1

Epitope mapping. Measured binding values are stated as relative luminescence units (RLU)

| Peptide | Sequence | Amino acid position (pre-PCT) | mAb 295/3H12 | mAb 295/4G9 | mAb 295/4G11 |
|---|---|---|---|---|---|
| PAD20 | SEQ ID NO: 6 | 25-44 | 36186 | 26496 | 30222 |
| PPD19 | SEQ ID NO: 7 | 26-44 | 182 | 310 | 297 |
| PFD18 | SEQ ID NO: 8 | 27-44 | 96 | 190 | 171 |
| PRD17 | SEQ ID NO: 9 | 28-44 | 65 | 158 | 164 |
| PSD16 | SEQ ID NO: 10 | 29-44 | 64 | 176 | 146 |
| Control | | | 61 | 149 | 162 |

I.4. Development of a Sandwich Immunoassay for Specific Measurement of PCT 1-116

I.4.1. Coupling

High-binding 5 ml polystyrene tubes (from Greiner) were coated as follows with a monoclonal antibody (internal designation: QN05) which is directed at an epitope in the C-terminal segment of procalcitonin and is also used in a commercial assay B.R.A.H.M.S PCT LIA: the antibody was diluted in 50 mM tris, 100 mM NaCl, pH 7.8, to a concentration of 6.6 μg/ml. 300 μl of this solution were pipetted into each tube. The tubes were incubated for 20 hours at 22° C. The solution was filtered with suction. Each tube was then filled with 4.2 ml of 10 mM sodium phosphate, 2% Karion FP, 0.3% bovine serum albumin, pH 6.5. After 20 hours, the solution was filtered with suction. Finally, the tubes were dried in a vacuum drier.

I.4.2. Marking

The monoclonal antibody mAb 295/3H12 which is characterized in more detail above with regard to its binding behaviour and specifically recognizes the N-terminus of PCT 1-116 was chemiluminescence-marked as described above under I.2.2.

I.4.3. Procedure and Evaluation of the Immunoassay

The peptide PAN40 (SEQ ID NO: 11), which was diluted serially in horse normal serum, served as standard material. Concentrations according to the peptide weight taken were ascribed to the standards thus prepared.

The sandwich immunoassay was prepared as follows: 50 μl of standards or samples and 150 μl of assay buffer (100 mM sodium phosphate, 150 mM NaCl, 0.5% bovine serum albumin, 0.1% unspecific mouse IgG, 0.1% sodium azide, pH 7.4), containing 0.5 million RFU (relative light units) of the MA70-marked antibody, were pipetted into the antibody-coated test tubes. Incubation was effected for 3 hours at 22° C. with shaking. This was followed by washing 4 times with 1 ml portions of wash solution (0.1% Tween 20) per tube, allowing to drip and measurement of the chemiluminescence bound to the tube in a luminometer (from BERTHOLD, LB952T; base reagents from BRAHMS AG). Using the software MultiCalc (Spline Fit), the PCT 1-116 concentrations of the samples were read from the standard curve. A typical standard curve is shown in FIG. 1. The test had a functional assay sensitivity (FAS), defined as the concentration at which the coefficient of variation of the mean of ten independent test runs was 20%, of 6 pmol/l.

Following the above-described experiments of the epitope specificity of the antibody 295/3H12, an investigation was carried out to determine the assay cross-reactivity for a peptide which was derived from procalcitonin and lacked the first N-terminal amino acid: A sample of PCT 2-116 (InVivo GmbH, Hennigsdorf, Germany; cf. also EP 1 408 334) having a concentration of 37433 pmol/l was measured as 206 pmol/l. The cross-reactivity was thus only 0.5%.

II. Measurements on the Analyte Stability and of Human Plasmas of Sepsis Patients II.1. Analyte Stability in Samples The stability of natural PCT 1-116 in samples from sepsis patients based on its measurability in the PCT 1-116 assay according to I., was first investigated. For this purpose, EDT plasma and serum samples were obtained from ten sepsis patients and then measured freshly and after storage for six hours at 22° C. by the abovementioned assay.

On average, the decrease in immunoreactivity after 6 h was only 3.6% in the case of the plasmas, and the largest individual decrease was 7.6%. In the case of the sera, on the other hand, the immunoreactivity decreased on average by 13.5%, and considerable individual differences in the decrease were observed.

The observed individual stability differences of PCT 1-116, in particular in serum, which reflect possibly individually different enzyme activity, mean that it may not be directly possible to relate measurable concentration changes of PCT 1-116 in an individual patient sample to a universally applicable reference value for the elimination of PCT 1-116 from the circulation, for example in order to distinguish cases of a pure decrease of a fixed starting concentration of PCT 1-116 from cases where a persistent or recurring secretion of PCT 1-116 is superposed on such a concentration decrease.

Procalcitonin, measured as PCT immunoreactivity or "PCT total" by the conventional B.R.A.H.M.S PCT LIA, is stable in serum samples after storage for six hours at 22° C. (operating instructions for B.R.A.H.M.S PCT LIA).

Figure 2:
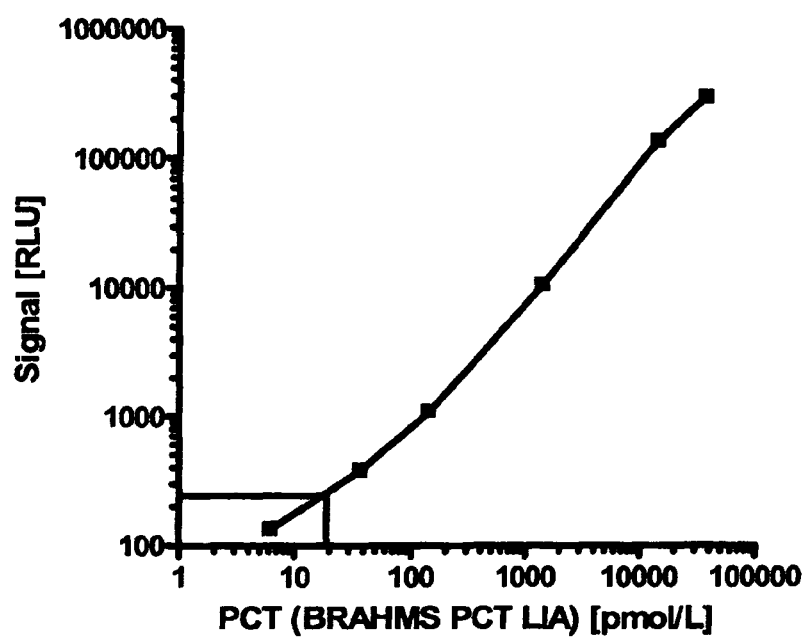
FIG. 2 shows a standard curve of a conventional B.R.A.H.M.S PCT LIA after adaptation of the calibration curve to the unit pmol/l.

The B.R.A.H.M.S PCT LIA is a sandwich immunoassay which uses monoclonal antibodies against epitopes in the C-terminal segment (katacalcin fraction) or mid-regional segment (calcitonin fraction). To permit a comparative consideration, the concentrations of the standards specified by the manufacturer in ng/ml were converted into pmol/l. A typical standard curve is shown in FIG. 2. The test had a functional assay sensitivity (FAS), defined as the concentration at which the coefficient of variation of the mean of ten independent test runs was 20%, of 20 pmol/l.

The determined stability of the analyte PCT 1-116 in human EDTA plasma can be regarded as being usually sufficient for clinical practice. However, if there is a risk that the respective EDTA plasma obtained from the sample cannot be measured at a sufficiently close time, it is within the scope of the present invention to prevent the degradation of the PCT 1-116 by dipeptidyl-aminopeptidase IV (DAP IV) to PCT 3-116 by addition of synthetic inhibitors for DAP IV to the sample (e.g. of Lys [Z($NO_2$)]-thiazolidide or of Pro-Pro$^{(P)}$ [OPh-4Cl]$_2$; cf. WRENGER S, KAHNE T, BOHUON C, WEGLÖHNER W, ANSORGE S, REINHOLD D: Aminoterminal truncation of procalcitonin, a marker for systemic bacterial infections, by dipeptidyl peptidase IV (DP IV), FEBS Lett 2000; 466:155-9). If, optionally additionally, other enzymes contribute to the decrease in the concentration of PCT 1-116 in a sample, it is of course also possible to use other inhibitors of the destructive enzyme effect.

II.2. Measurements on Clinical Value

II.2.1. Kinetics of Successful Treatment of Infections

It is desirable to recognize the success of the treatment in the case of sepsis patients early and reliably because the safety in the treatment regime of a patient is increased thereby and expensive stays in the intensive care unit can be reduced.

For checking the question as to whether the measurement, according to the invention, of PCT 1-116 with the use of the sandwich assay described above can give results which differ from those of a conventional measurement of the PCT immunoreactivity ("PCT total"), the following procedure was adopted:

Plasma samples were obtained daily from eight sepsis patients who were successfully treated in the intensive care unit. PCT total (measured by the conventional B.R.A.H.M.S PCT LIA; see above) and PCT 1-116 were measured at the beginning of the treatment and on the two subsequent days. The median concentrations at the beginning of the measurements (on day 0) were 100.6 pmol/l for PCT 1-116 and 591.8 pmol/l for PCT total (molar ratio of the initial concentrations of about 0.17).

Figure 3:
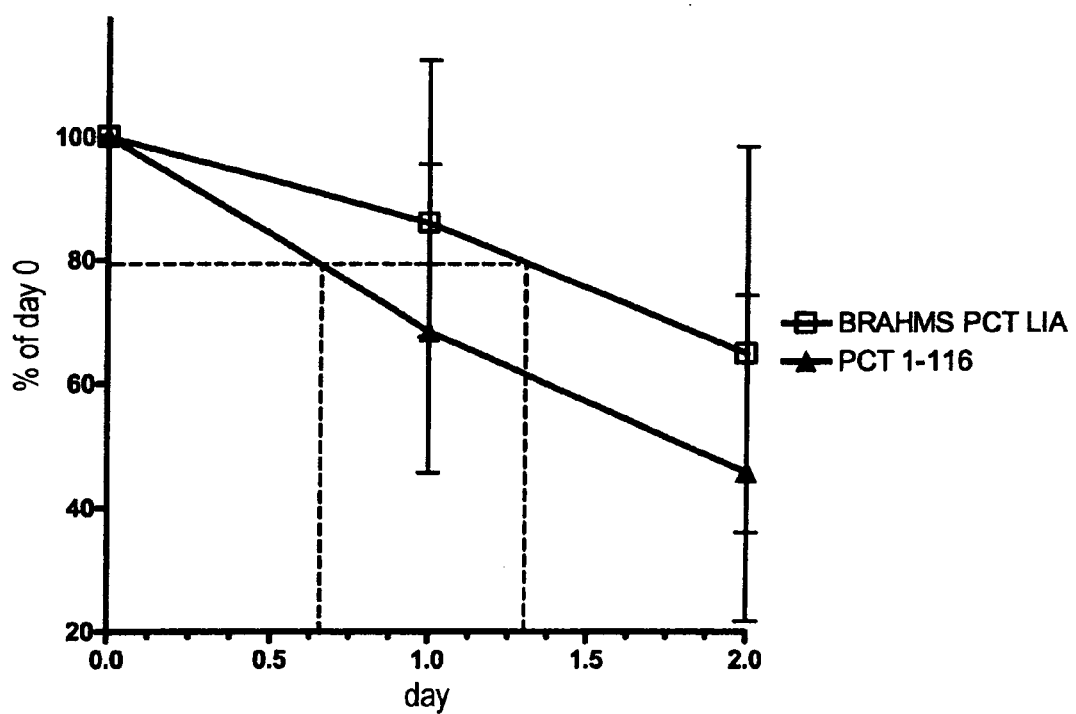
FIG. 3 shows comparative measurements of the change in the concentration of PCT 1-116 by the assay according to the invention (triangles) and the concentration of PCT total by a commercial assay (B.R.A.H.M.S PCT LIA; squares), based in each case on the coordinated starting concentrations on day 0 and measured in EDTA plasmas of eight successfully treated sepsis patients of an intensive care ward.

The concentrations of PCT 1-116 decreased significantly more rapidly than those of PCT total: the decrease of PCT 1-116, based on day 0, was 32% on the first day and 52% on the second day. In contrast, the decrease of PCT total was only 11% on the first day and only 30% on the second day (FIG. 3).

In view of the diagnostic aim of recognizing the successful treatment as quickly as possible on the basis of a decrease in the procalcitonin secretion, it is now possible to pose the question concerning the time after which the two assay methods compared above enable a decrease to be recognized at all. If inter assay variances are taken into account, it is approximately true, that a decrease of about 20% can be classed as being reliably detectable. Such a decrease is detectable after only 0.6 day in a measurement of PCT 1-116, but only after 1.2 days in the conventional measurement of the PCT immunoreactivity (of PCT total).

The success of a treatment is therefore substantially more quickly and reliably detectable in the measurement of PCT 1-116 than in the conventional measurement of the PCT immunoreactivity ("PCT total").

Figure 4:
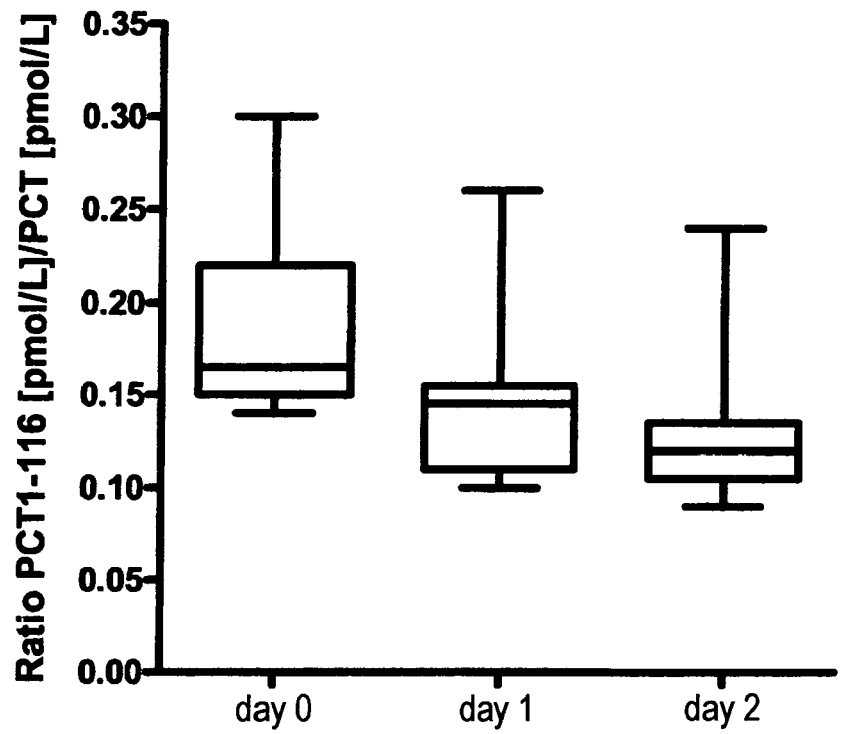
FIG. 4 shows results of the determination of the molar ratio of PCT 1-116 to PCT total in samples according to FIG. 3 and the change thereof as a function of time in the course of 3 days.

For a further evaluation of the measured data, the respective molar ratio of PCT 1-116 to PCT total was calculated for each patient and each measuring time. Over the three days of observation, this ratio, expressed as the median, decreased from 0.17 through 0.15 to 0.12 (FIG. 4). This evaluation, too, reflects the different degradation kinetics of PCT 1-116 and PCT total. Expressed simply, it is true that the decrease of PCT 1-116 directly reflects the degradation thereof or lower stability, while the decrease of "PCT total" reflects the degradation of PCT 3-116 or the stability thereof. Since the conversion of PCT 1-116 into PCT 3-116 should not have a substantial effect on the measurement in the determination of PCT total because the conventional method does not distinguish between PCT 1-116 and PCT 3-116, the rate of conversion of PCT 1-116 into PCT 3-116 does not significantly influence the decrease in concentration of PCT total, so that this substantially corresponds to the decrease of the more stable PCT 3-116 which has accumulated in the sample.

The above considerations show that moreover a small value for the ratio of PCT 1-116 to PCT total (i.e. a low concentration of PCT 1-116 at a simultaneously comparatively high concentration of PCT total) indicates the end of the infection, while a large value indicates a time close to the beginning of the PCT secretion and hence a highly acute infection. This observation has implications not only for observation of the progression but also for the initial estimation of the infection status of a patient, for example at emergency admission or on medical treatment as an outpatient.

II.2.2. Kinetics in the Case of Secondary Infection

During their stay in the intensive care unit, sepsis patients frequently suffer a further infection which, owing to the weakened immune system, is particularly life-threatening and can have fatal effects. The earlier such a secondary infection is detected, the more quickly and effectively can therapeutic countermeasures be initiated. Owing to the known phenomenon of endotoxin tolerance, however, secondary infections result in a less pronounced increase in the PCT total concentration.

The early detection of a bacterial reinfection which is associated with a less pronounced subsequent increase in the temporarily already reduced or even terminated PCT secretion is particularly complicated in that, owing to the primary infection, the patients already have considerable PCT total concentrations which, due to the high stability of PCT 3-116, are only relatively slowly reduced even with successful treatment. As was shown above, PCT 1-116 has substantially faster in vivo degradation kinetics than PCT total (with a predominant proportion of PCT 3-116). If it is assumed that PCT 1-116 is converted in the first step of its degradation into PCT 3-116, the decrease in the concentration (lower in absolute values) of PCT 1-116 does not correspond to an increase in the values for PCT total. These increase only at the rate of production of fresh PCT 1-116.

In the case of an infection which has been substantially withstood and is no longer acute—i.e. before a secondary infection—the measurable concentrations of PCT 1-116 should be relatively low, although absolute values for the concentrations of PCT total are still high owing to the stability of PCT 3-116, which at this time is likely to make the main contribution to the measured concentration of PCT total. A subsequent increase in the PCT secretion, induced by a secondary infection, should therefore be detectable at an early stage on the basis of the measured values for PCT 1-116, whereas it is not detectable or not unambiguously detectable on the basis of the very much higher measured values for PCT total in absolute terms.

The consideration of the PCT 1-116 and PCT 3-116 concentrations measured together in the determination of PCT total leads to the conclusion that, under the influence of a fairly slow decrease of a high concentration of PCT 3-116 from the primary infection and the subsequent increase of PCT from the secondary infection, the beginning of the resecretion of PCT is possibly detectable not immediately as a measurable increase of the total PCT but initially only as a poorly detectable reduction of the decrease of the PCT total concentrations, which being to decrease more slowly than corresponds to the clearing rate of PCT 3-116.

An investigation was therefore carried out to determine whether a concentration development of PCT 1-116 in the sense of an increase or slowing down below the usual stability-related concentration reduction of PCT 1-116, which differs substantially from the concentration development of PCT total, predicts a subsequent increase also of PCT total on the subsequent day—as a sign of a secondary infection.

Plasma was obtained daily from 44 sepsis patients with an average stay of 10.8 days in the intensive care unit, PCT total and PCT 1-116 were determined in parallel in said plasma, and the concentration curve thereof was monitored for each individual patient during the period of the measurements.

It was observed six times that an increase of PCT total on the subsequent day was preceded by an increase of PCT 1-116, while PCT total still declined.

In 7 other cases—in each case with continuing decrease of PCT total—a reduced reduction of the decrease of the concentration of PCT 1-116, i.e. a slower decrease than in other samples, was observed, which was associated with the onset of a secondary infection. The concentrations of PCT total did not yet change to a significant extent. Only on the subsequent day were signs of a subsequent increase of PCT total detectable. It is within the scope of the present invention also to use those "hidden" increases of the concentration of PCT 1-116, which are not yet manifest in the monitoring of PCT total, with the application of suitable monitoring and evaluation techniques and mathematical models suitable for this purpose in the monitoring of therapeutic sepsis patients for detecting secondary infections.

In summary, it may be said that a PCT 1-116 decrease which is reduced compared with PCT total or even an increase of PCT 1-116 on the subsequent day predicts in a highly specific and even sensitive manner an increase of PCT total as an expression of a secondary infection.

In view of the results disclosed above, the inventors contemplate the selective determination of PCT 1-116 according to the method of the present invention as alternative to the determination of PCT(total) by an assay recognizing predominantly PCT 3-116. PCT 1-116 can be determined in all cases in which the determination of PCT(total) has already proved to be useful in the field of medical diagnosis.

In particular, the use of the selective determination of PCT 1-116 for the diagnosis, differential diagnosis, risk stratification, prognosis, assessment of the course of a disease and the control of therapeutic measures is intended or contemplated especially for human patients in connection with infections, especially infections by gram-negative or gram-positive bacteria and by fungal and/or parasitic etiological agents, which infections may cause a locally confined or systemic inflammatory response (for example sepsis, severe sepsis and septic shock), as well as in cases of an underlying co-morbidity in heart failure patients, and, further, for the purpose of risk stratification and prognosis of patients suffering from coronary artery disease (CAD).

The invention claimed is:

1. An isolated antibody which specifically binds an epitope of procalcitonin 1-116, said epitope comprising amino acids 1 and 2 of procalcitonin 1-116, and binds selectively to intact procalcitonin 1 to 116 (SEQ ID NO: 1) or procalcitonin partial peptides comprising amino acids 1 and 2 of SEQ ID NO: 1, but does not bind to procalcitonin partial peptides that do not include amino acids 1 and 2 of SEQ ID NO: 1.

2. The isolated antibody of claim 1, which is obtainable by immunisation of an animal with an antigen, in the form of a conjugate with a peptide which is or comprises a peptide according to SEQ ID NO: 4.

3. The isolated antibody of claim 1, wherein said antibody is a monoclonal antibody.

4. An isolated antibody which specifically binds a peptide consisting of the amino acid sequence of amino acids 1-9 of SEQ ID NO: 1, wherein said antibody binds selectively to intact procalcitonin$_{1\ to\ 116}$ (SEQ ID NO: 1) or procalcitonin partial peptides comprising amino acids 1 and 2 of SEQ ID NO: 1, but does not bind to procalcitonin partial peptides that do not include amino acids 1 and 2 of SEQ ID NO: 1.

* * * * *

SEQUENCE LISTING

```
<160> NUMBER OF SEQ ID NOS: 11

<210> SEQ ID NO 1
<211> LENGTH: 116
<212> TYPE: PRT
<213> ORGANISM: HUMAN

<400> SEQUENCE: 1

Ala Pro Phe Arg Ser Ala Leu Glu Ser Ser Pro Ala Asp Pro Ala Thr
1               5                   10                  15

Leu Ser Glu Asp Glu Ala Arg Leu Leu Leu Ala Ala Leu Val Gln Asp
                20                  25                  30

Tyr Val Gln Met Lys Ala Ser Glu Leu Glu Gln Glu Gln Glu Arg Glu
            35                  40                  45

Gly Ser Ser Leu Asp Ser Pro Arg Ser Lys Arg Cys Gly Asn Leu Ser
        50                  55                  60

Thr Cys Met Leu Gly Thr Tyr Thr Gln Asp Phe Asn Lys Phe His Thr
65                  70                  75                  80

Phe Pro Gln Thr Ala Ile Gly Val Gly Ala Pro Gly Lys Lys Arg Asp
                85                  90                  95

Met Ser Ser Asp Leu Glu Arg Asp His Arg Pro His Val Ser Met Pro
                100                 105                 110

Gln Asn Ala Asn
            115

<210> SEQ ID NO 2
<211> LENGTH: 114
<212> TYPE: PRT
<213> ORGANISM: HUMAN
```

-continued

```
<400> SEQUENCE: 2

Phe Arg Ser Ala Leu Glu Ser Ser Pro Ala Asp Pro Ala Thr Leu Ser
1               5                   10                  15

Glu Asp Glu Ala Arg Leu Leu Ala Ala Leu Val Gln Asp Tyr Val
            20                  25                  30

Gln Met Lys Ala Ser Glu Leu Glu Gln Glu Gln Arg Glu Gly Ser
        35                  40                  45

Ser Leu Asp Ser Pro Arg Ser Lys Arg Cys Gly Asn Leu Ser Thr Cys
    50                  55                  60

Met Leu Gly Thr Tyr Thr Gln Asp Phe Asn Lys Phe His Thr Phe Pro
65                  70                  75                  80

Gln Thr Ala Ile Gly Val Gly Ala Pro Gly Lys Lys Arg Asp Met Ser
                85                  90                  95

Ser Asp Leu Glu Arg Asp His Arg Pro His Val Ser Met Pro Gln Asn
            100                 105                 110

Ala Asn

<210> SEQ ID NO 3
<211> LENGTH: 139
<212> TYPE: PRT
<213> ORGANISM: Artificial
<220> FEATURE:
<223> OTHER INFORMATION: Synthetic

<400> SEQUENCE: 3

Met Gly Phe Gln Lys Phe Ser Pro Phe Leu Ala Leu Ser Ile Leu Val
1               5                   10                  15

Leu Leu Gln Ala Gly Ser Leu His Ala Ala Pro Phe Arg Ser Ala Leu
            20                  25                  30

Glu Ser Ser Pro Ala Asp Pro Ala Thr Leu Ser Asp Glu Ala Arg Leu
        35                  40                  45

Leu Ala Ala Leu Val Gln Asp Tyr Val Gln Met Lys Ala Ser Glu Leu
    50                  55                  60

Glu Gln Glu Gln Glu Arg Glu Gly Ser Ser Leu Asp Ser Pro Arg Ser
65                  70                  75                  80

Lys Arg Cys Gly Asn Leu Ser Thr Cys Met Leu Gly Thr Tyr Thr Gln
                85                  90                  95

Asp Phe Asn Lys Phe His Thr Phe Pro Gln Thr Ala Ile Gly Val Gly
            100                 105                 110

Ala Pro Gly Lys Lys Arg Asp Met Ser Ser Asp Leu Glu Arg Asp His
        115                 120                 125

Arg Pro His Val Ser Met Pro Gln Asn Ala Asn
    130                 135

<210> SEQ ID NO 4
<211> LENGTH: 10
<212> TYPE: PRT
<213> ORGANISM: Artificial
<220> FEATURE:
<223> OTHER INFORMATION: Synthetic

<400> SEQUENCE: 4

Ala Pro Phe Arg Ser Ala Leu Glu Ser Cys
1               5                   10

<210> SEQ ID NO 5
<211> LENGTH: 21
<212> TYPE: PRT
<213> ORGANISM: Artificial
```

```
<220> FEATURE:
<223> OTHER INFORMATION: Synthetic

<400> SEQUENCE: 5

Ala Ala Pro Phe Arg Ser Ala Leu Glu Ser Ser Pro Ala Asp Pro Ala
1               5                   10                  15

Thr Leu Ser Glu Asp
            20

<210> SEQ ID NO 6
<211> LENGTH: 20
<212> TYPE: PRT
<213> ORGANISM: Artificial
<220> FEATURE:
<223> OTHER INFORMATION: Synthetic

<400> SEQUENCE: 6

Ala Pro Phe Arg Ser Ala Leu Glu Ser Ser Pro Ala Asp Pro Ala Thr
1               5                   10                  15

Leu Ser Glu Asp
            20

<210> SEQ ID NO 7
<211> LENGTH: 19
<212> TYPE: PRT
<213> ORGANISM: Artificial
<220> FEATURE:
<223> OTHER INFORMATION: Synthetic

<400> SEQUENCE: 7

Pro Phe Arg Ser Ala Leu Glu Ser Ser Pro Ala Asp Pro Ala Thr Leu
1               5                   10                  15

Ser Glu Asp

<210> SEQ ID NO 8
<211> LENGTH: 18
<212> TYPE: PRT
<213> ORGANISM: Artificial
<220> FEATURE:
<223> OTHER INFORMATION: Synthetic

<400> SEQUENCE: 8

Phe Arg Ser Ala Leu Glu Ser Ser Pro Ala Asp Pro Ala Thr Leu Ser
1               5                   10                  15

Glu Asp

<210> SEQ ID NO 9
<211> LENGTH: 17
<212> TYPE: PRT
<213> ORGANISM: Artificial
<220> FEATURE:
<223> OTHER INFORMATION: Synthetic

<400> SEQUENCE: 9

Arg Ser Ala Leu Glu Ser Ser Pro Ala Asp Pro Ala Thr Leu Ser Glu
1               5                   10                  15

Asp

<210> SEQ ID NO 10
<211> LENGTH: 16
<212> TYPE: PRT
<213> ORGANISM: Artificial
<220> FEATURE:
<223> OTHER INFORMATION: Synthetic
```

```
<400> SEQUENCE: 10

Ser Ala Leu Glu Ser Ser Pro Ala Asp Pro Ala Thr Leu Ser Glu Asp
1               5                   10                  15

<210> SEQ ID NO 11
<211> LENGTH: 40
<212> TYPE: PRT
<213> ORGANISM: Artificial
<220> FEATURE:
<223> OTHER INFORMATION: Synthetic

<400> SEQUENCE: 11

Ala Pro Phe Arg Ser Ala Leu Glu Ser Ser Pro Ala Asp Pro Ala Thr
1               5                   10                  15

Leu Ser Glu Asp Met Ser Ser Asp Leu Glu Arg Asp His Arg Pro His
            20                  25                  30

Val Ser Met Pro Gln Asn Ala Asn
        35                  40
```